(12) United States Patent
Faubert et al.

(10) Patent No.: US 9,872,635 B2
(45) Date of Patent: Jan. 23, 2018

(54) METHOD FOR MEASURING THE VISUALLY-INDUCED POSTURAL INSTABILITY OF A PERSON

(71) Applicants: ESSILOR CANADA LTEE, Ville Saint-Laurent (CA); Université de Montréal, Montreal (CA)

(72) Inventors: Jocelyn Faubert, Montreal (CA); Guillaume Giraudet, Montreal (CA); Rafael Doti, Montreal (CA); Eduardo Lugo, Laval (CA)

(73) Assignees: Essilor Canada Ltee, Ville Saint-Laurent (CA); Université de Montréal, Montreal (CA)

( * ) Notice: Subject to any disclaimer, the term of this patent is extended or adjusted under 35 U.S.C. 154(b) by 0 days.

(21) Appl. No.: 14/428,802

(22) PCT Filed: Sep. 11, 2013

(86) PCT No.: PCT/CA2013/050699
§ 371 (c)(1),
(2) Date: Mar. 17, 2015

(87) PCT Pub. No.: WO2014/040186
PCT Pub. Date: Mar. 20, 2014

(65) Prior Publication Data
US 2015/0230732 A1   Aug. 20, 2015

(30) Foreign Application Priority Data

Sep. 17, 2012 (EP) .................................... 12184731

(51) Int. Cl.
*A61B 3/14* (2006.01)
*A61B 3/00* (2006.01)
(Continued)

(52) U.S. Cl.
CPC .............. *A61B 5/103* (2013.01); *A61B 3/113* (2013.01); *A61B 5/11* (2013.01)

(58) Field of Classification Search
CPC ............ A61B 5/103; A61B 3/113; A61B 5/11
(Continued)

(56) References Cited

FOREIGN PATENT DOCUMENTS

| EP | 2095759 | 9/2009 |
|----|---------|--------|
| EP | 2198770 | 6/2010 |

OTHER PUBLICATIONS

Borger, LL, et al., The influence of dynamic visual environments on postural sway in the elderly, *J. Vestib. Res.*, 1999, vol. 9(3), pp. 197-205.

(Continued)

*Primary Examiner* — Jack Dinh
(74) *Attorney, Agent, or Firm* — Gardere Wynne Sewell LLP

(57) ABSTRACT

Method for measuring the visually-induced postural instability of a person is described, the method comprising a display providing step (S1) during which a visual display device is provided. The display device is arranged so as to display a dynamic visual pattern in at least 50% of the lower half of the visual field of the person, leaving an upper half of the visual field of the person free. The method also comprises a display step (S2) during which a dynamic visual pattern is displayed on the visual display device. The method further comprises a measuring step (S3) during which a parameter representative of the postural instability is measured when the person is gazing at a fix target straight in front while having the dynamic visual pattern displayed on the visual display device.

17 Claims, 3 Drawing Sheets

(51) Int. Cl.
*A61B 5/103* (2006.01)
*A61B 3/113* (2006.01)
*A61B 5/11* (2006.01)

(58) Field of Classification Search
USPC .................................................. 351/209, 246
See application file for complete search history.

(56) References Cited

OTHER PUBLICATIONS

Slobounov S, et al., Neural underpinning of postural responses to visual field motion, *Biol. Psychol.*, May 2006, vol. 72(2), pp. 188-197. Epub. Dec. 9, 2005.

Jeka, J, et al., Sensory reweighting with translational visual stimuli in young and elderly adults: the role of state-dependent noise, *Exp. Brain Res.*, Oct. 2006, vol. 174(3), pp. 517-527. Epub. May 23, 2006.

Simeonov, P, et al., Postural stability effects of random vibration at the feet of construction workers in simulated elevation, *Appl. Ergon.*, Jul. 2011, 42(5), pp. 672-81. Epub. Nov. 2010.

Agarwal, K, et al. Visual dependence and BPPV, *J. Neurol.*, Jun. 2012, vol. 259(6), pp. 1117-1124. Epub. Nov. 24, 2011.

Laurens, J, et al., Visual contribution to postural stability: Interaction between target fixation or tracking and static or dynamic large-field stimulus, *Gait & Posture*, 2010, vol. 31, pp. 37-41.

Borger, LL, et al., The influence of dynamic visual environments on postural sway in the elderly, *J. Vestib. Res.*, 1999, vol. 9(3), pp. 197-205. Abstract only.

Guskiewicz, KM, et al., Postural stability and neuropsychological deficits after concussion in collegiate athletes, *Journal of Athletic Training*, Sep. 2001, vol. 36(3), pp. 263-273.

Ustinova, KI, et al., Gaze and viewing angle influence visual stabilization of upright posture, *Brain and Behavior*, 2011, pp. 1-7.

Lasley DJ, et al., Postural stability and stero-ambiguity in man-designed visual environments, *IEEE Tansactions on Biomedical Engineering*, vol. 38(8), Aug. 1991, pp. 808-813.

O'Connor, KW, et al., Postural adapations to repeated optic flow stimulation in older adults, *Gait Posture*, Oct. 2008, vol. 28(3), pp. 385-391.

Slobounov S, et al., Neural underpinning of postural responses to visual field motion, *Biol. Psychol.*, May 2006, vol. 72(2), pp. 188-197. Epub. Dec. 2009. Abstract only.

Jeka, J, et al., Sensory reweighting with translational visual stimuli in young and elderly adults: the role of state-dependent noise, *Exp. Brain Res.*, Oct. 2006, vol. 174(3), pp. 517-527. Epub. May 2006. Abstract only.

Simeonov, P, et al., Postural stability effects of random vibration at the feet of construction workers in simulated elevation, *Appl. Ergon.*, Jul. 2011, 42(5), pp. 672-81. Epub. Nov. 2010. Abstract only.

Dearing, RR, et al., The contribution of different parts of the visual field to the perception of upright, *Vision Research*, Aug. 2011, vol. 51, pp. 2207-2215.

Agarwal, K, et al. Visual dependence and BPPV, *J. Neurol.*, Jun. 2012, vol. 259(6), pp. 1117-1124. Epub. Nov. 2011. Abstract only.

International Preliminary Report on Patentability and Written Opinion of the International Searching Authority for International Application No. PCT/CA213/050699, dated Mar. 17, 2015, (5 pages).

Extended European Search Report and European Search Opinion, dated Feb. 13, 2013, for European Application No. 12184731.3 (8 pages).

METHOD FOR MEASURING THE VISUALLY-INDUCED POSTURAL INSTABILITY OF A PERSON

CROSS REFERENCE TO RELATED APPLICATIONS

This application is a U.S. national stage application of International Application No. PCT/CA2013/050699 filed Sep. 11, 2013, which claims the benefit of priority to EP Application No. 12184731.3, filed Sep. 17, 2012; the entirety of each of said applications is incorporated herein by reference.

FIELD OF THE INVENTION

The invention relates to a method for measuring the visually-induced postural instability of a person and a method for measuring the effect of a pair of spectacle lenses on body posture stability/instability of a wearer. The invention further relates to a computer program product and computer readable medium carrying one or more sequences of instructions of the computer program product of the invention.

BACKGROUND

It is known that individuals have different postural instability. In particular, each individual has a different visually-induced postural instability. In other words, it is known that an individual has a specific postural reaction to a given visual instability.

Prior art methods for measuring the visually-induced postural instability comprised using a cave automatic virtual environment (better known by the recursive acronym CAVE) consisting of an immersive virtual reality environment where projectors are directed to at least four walls of a room-sized cube. Such experimental environment provides interesting results. However, a CAVE system is very expensive, requires very sophisticated hardware and software and has large overall dimensions. Furthermore, such prior art methods require highly skilled professional to be implemented. Thus, such methods cannot be implemented on a large scale.

The discussion of the background of the invention herein is included to explain the context of the invention. This is not to be taken as an admission that any of the material referred to was published, known or part of the common general knowledge, as at the priority date of any of the claims.

A goal of the invention described herein is to propose a method for measuring the visually-induced postural instability that does not present the drawbacks of the prior art methods, in particular described herein is an easily implemented method of measuring the visual-induced postural instability, for example, for a person having to wear ophthalmic lenses.

SUMMARY

To this end, the invention described herein proposes a method for measuring the visually-induced postural instability of a person, the method comprising:
 a display providing step during which a visual display device is provided and arranged so as to display a dynamic visual pattern in at least 50% of the lower half visual field of the person and to leave the upper half visual field of the person free,
 a display step during which a dynamic visual pattern is displayed on the visual display device,
 a measuring step during which a parameter representative of the postural instability is measured when the person is gazing at a fixed target straight in front of him while having the dynamic visual pattern displayed on the visual display device.

Advantageously, the method according to the invention can easily be implemented. Indeed, the inventors have observed that most of the visually-induced postural instability is induced by visual stimuli in the lower half visual field of a person. Thus, according to the method of the invention the visually-induced postural instability is measured by providing visual stimuli only in part of the lower half visual field. Thus, the method can be implemented very easily using for example a screen placed in the lower half visual field of a person and the implementation of the method allows using a visual display device having reduced overall dimensions compared to the prior art solutions.

Further embodiments, which can be considered alone or in combination, include:
 the dynamic visual pattern is displayed with a movement of translation along or rotation around an axis perpendicular to the vertical axis, and/or
 the dynamic visual pattern has an oscillation movement, and/or
 the dynamic visual pattern has a periodic movement, and/or
 the dynamic visual pattern comprises a checkerboard pattern, and/or
 the visual display device comprises a reflective screen, for example a mirror, placed in the lower half visual field of the person, the visual display device being arranged so that the person sees the dynamic visual pattern on the reflective screen, and/or
 the visual display device comprises a semi-transparent diffusive screen placed in the lower half visual field of the person, and/or
 the visual display device comprises a dynamic visual pattern generating device adapted to generate a dynamic visual pattern and a projecting device adapted to project the generated dynamic visual pattern on the semi-transparent screen, and/or
 the reflectivity of the semi-transparent screen is greater than or equal to 1% and smaller than or equal to 50%, and/or
 the semi-transparent screen is curved so as to have a conic transversal shape, and/or
 the visual display device comprises an active photonic screen placed in the lower half visual field of the person and arranged to display the dynamic visual pattern.

According to another aspect, the invention relates to a method for measuring effect of a pair of spectacle lenses on body posture stability/instability of a wearer comprising measuring the visually-induced postural instability of a wearer wearing the pair of spectacle lenses using the method according to the invention.

According to a further aspect, the invention relates to a computer program product comprising one or more stored sequence of instruction that is accessible to a processor and which, when executed by the processor, causes the processor to process at least on device to carry out the steps of the method according to the invention.

Furthermore, the invention relates to a computer readable medium carrying one or more sequences of instructions of the computer program product according to the invention.

Unless specifically stated otherwise, as apparent from the following discussions, it is appreciated that throughout the specification discussions utilizing terms such as "computing", "calculating", "generating", or the like, refer to the action and/or processes of a computer or computing system, or similar electronic computing device that manipulate and/or transform data represented as physical, such as electronic, quantities within the computing system's registers and/or memories into other data similarly represented as physical quantities within the computing system's memories, registers or other such information storage, transmission or display devices.

Embodiments described herein may include apparatuses for performing the operations herein. These apparatuses may be specially constructed for the desired purposes, or may comprise a general purpose computer or Digital Signal Processor ("DSP") selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems will appear from the description below. In addition, the described embodiments are not described with reference to any particular programming language. It will be appreciated that a variety of programming languages may be used to implement the teachings of the inventions as described herein.

BRIEF DESCRIPTION OF THE DRAWINGS

Other features and advantages of the present invention will become apparent from the following description of non-limitative embodiments, with reference to the attached drawings in which.

DESCRIPTION

In the sense of what is described herein, a semi-transparent screen has a reflectivity greater than or equal to 1%, for example greater than or equal to 5% and smaller than or equal to 50%, for example, smaller than or equal to 15%, for example, substantially equal to 10%.

In the sense of the invention, the lower half visual filed refers to the part of the visual filed of a person gazing at a fixed target situated below the plan defined by the person's eyes and the fixed target.

Figure 1:
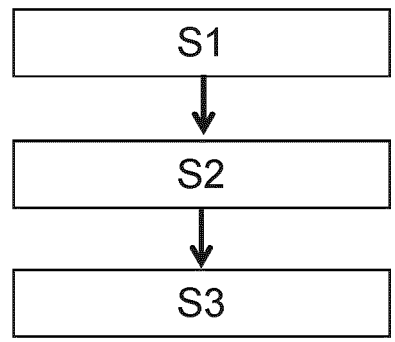
FIG. 1 is a flowchart representing different steps of a method according to the invention.

According to an embodiment of the invention illustrated on FIG. 1, the method for measuring the visually-induced postural instability of a person is depicted, the method comprising:

a display providing step S1, a display step S2, and a measuring step S3.

A visual display device is provided during the visual display providing step S1.

The visual display device is arranged so as to display a dynamic visual pattern in at least 50% of the lower half of a visual field of the person under test and to leave the upper half of the visual field of the person free.

The inventors have observed that the visually-induced postural instability of an individual is mostly influence by visual changes in his lower half visual field. Therefore, the method according to the invention may use a display device arranged to display a dynamic visual pattern only in the lower half visual field, leaving the upper half of the visual field of the person free. Advantageously, the method uses a much cheaper and more easy to handle visual display device than the prior art methods.

Furthermore, the inventors have observed having the dynamic visual pattern displayed in only 50% of the lower visual field provides measurable visually-induced postural instability.

Thus, the method according to the invention may use a visual display device arranged to display a dynamic visual pattern only in part of the lower half of the visual field, for example, in at least 50% of the lower visual filed.

According to an embodiment described herein, the visual display device is arranged to display a dynamic visual pattern within the binocular visual zone of the lower half of the visual field. According to a further embodiment described herein, the visual display device is arranged to display a dynamic visual pattern in at least 75% of the lower half of the visual field of the person under test.

According to an embodiment described herein, the visual display device comprises a reflecting screen placed in the lower half of the visual field of the person, the visual display device being arranged so that the person sees the dynamic visual pattern on the reflecting screen. The reflecting screen may be a mirror or a semi-transparent mirror.

Figure 2:
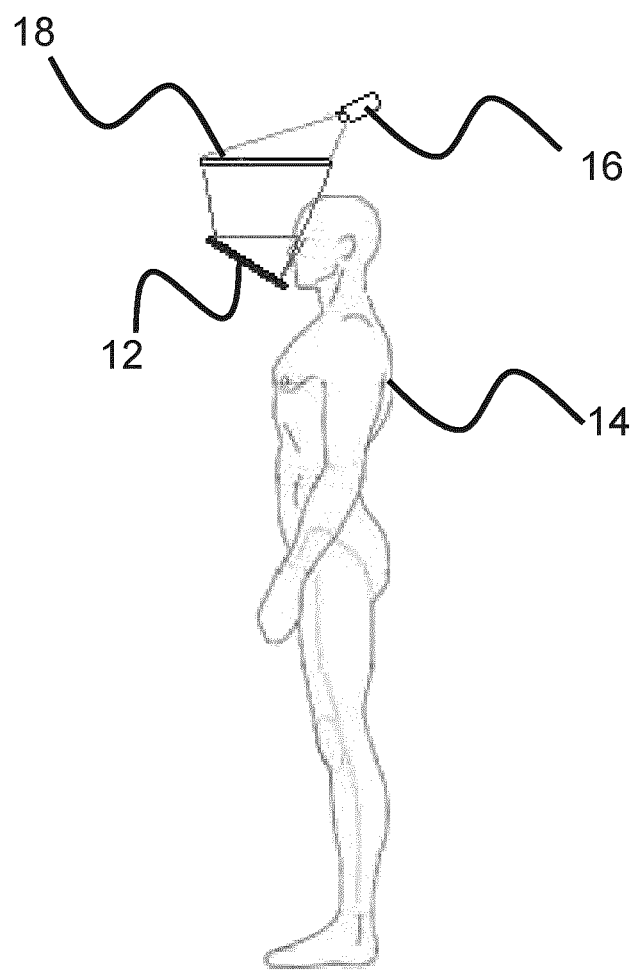
FIG. 2 illustrates a person using a display device according to a first embodiment of the invention.

An example of such an embodiment is illustrated on FIG. 2, where the display device 10 comprises a plan mirror 12 provided in the lower half visual field of the person under test 14. The plan mirror 12 is arranged so as to reflect the image projected by a projector 16 on an intermediate screen 18. The projector 16 and the intermediate screen 14 should be placed out of the visual field of the person or masked, for example over the person's head or at ground level.

According to such embodiment, the plan mirror 12 may be a full reflective mirror or a semi-transparent mirror.

Advantageously, the use of such visual display device is very cheap and easy to use. Indeed, the different elements of the display device are commonly available elements.

Advantageously, the use of a semi-transparent mirror as a reflective screen increases the immersion effect for the person under test. Indeed, the use of a semi-transparent mirror makes it possible for the person under test to see the background scene in his lower half visual field through the semi-transparent mirror.

Advantageously, the described display device is conceived to add to the natural surrounding image perceived by the person under test, a luminance perturbing dynamic visual pattern, i.e., perceived luminance modulation, so as to measure the person's balance resilience in this condition or with the display device in operation.

Figure 3:
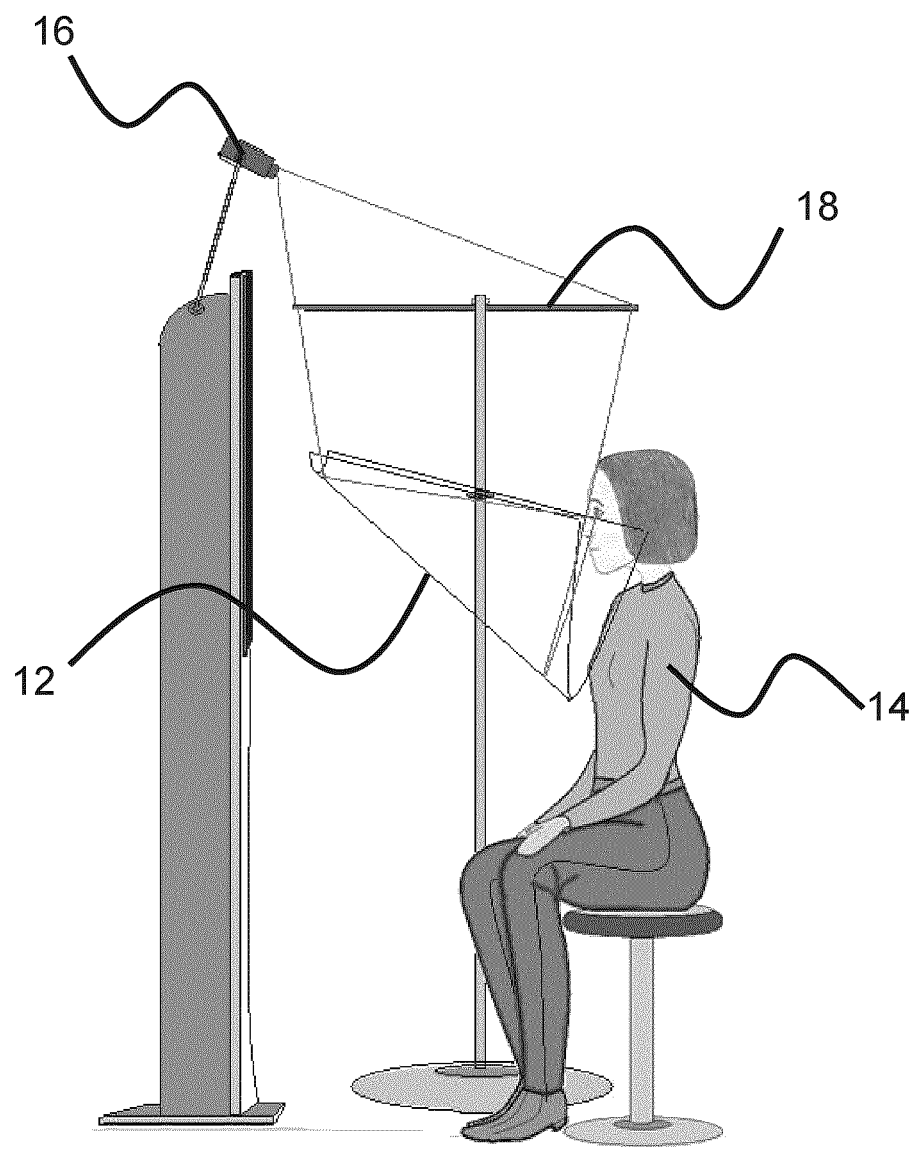
FIG. 3 illustrates a person using a display device according to a second embodiment of the invention.

A further example of such embodiment is illustrated on FIG. 3, where the visual display device display is similar to the visual display represented on FIG. 2. The visual display device comprises a reflective screen 12 provided in the lower half visual field of the person under test 14. The reflective screen 12 is arranged so as to reflect the image projected by a projector 16 on an intermediate screen 18. As in the embodiment of FIG. 2, the projector 16 and the intermediate screen are out of the visual field of the person or masked.

As for the visual display device of FIG. 2, the reflective screen 12 may be fully reflective or semi-transparent.

The semi-transparent screen 12 may be a high transparent plastic sheets with a high quality surface finishing, such as polycarbonate sheets, oriented PET films, rigid PVC film, cellulose acetate film, or polyethylene sheet (HDPE).

The reflective screen 12 represented on FIG. 3, is curved so as to have a conic transversal shape. For example the semi-transparent screen 12 has an elliptic transversal shape.

Advantageously, the use of such shaped reflective screen 12 allows for a reduction in the overall dimensions of the visual display device. In other words, reducing the overall dimension of such shaped reflective screen 12 allows for an increase in the immersion effect for the person under test. Furthermore, such conic transversal shape increases the mechanic stability of the screen.

Furthermore, the use of an at least partially transparent reflective screen increases the sensory conflicts, thus, increases the visually-induced postural instability of the person.

According to an embodiment described herein, the visual display device comprises a semi-transparent diffusive screen placed in the lower half of the visual field of the person, the visual display device being arranged so that the person sees the dynamic visual pattern on the semi-transparent diffusive screen.

Figure 4:
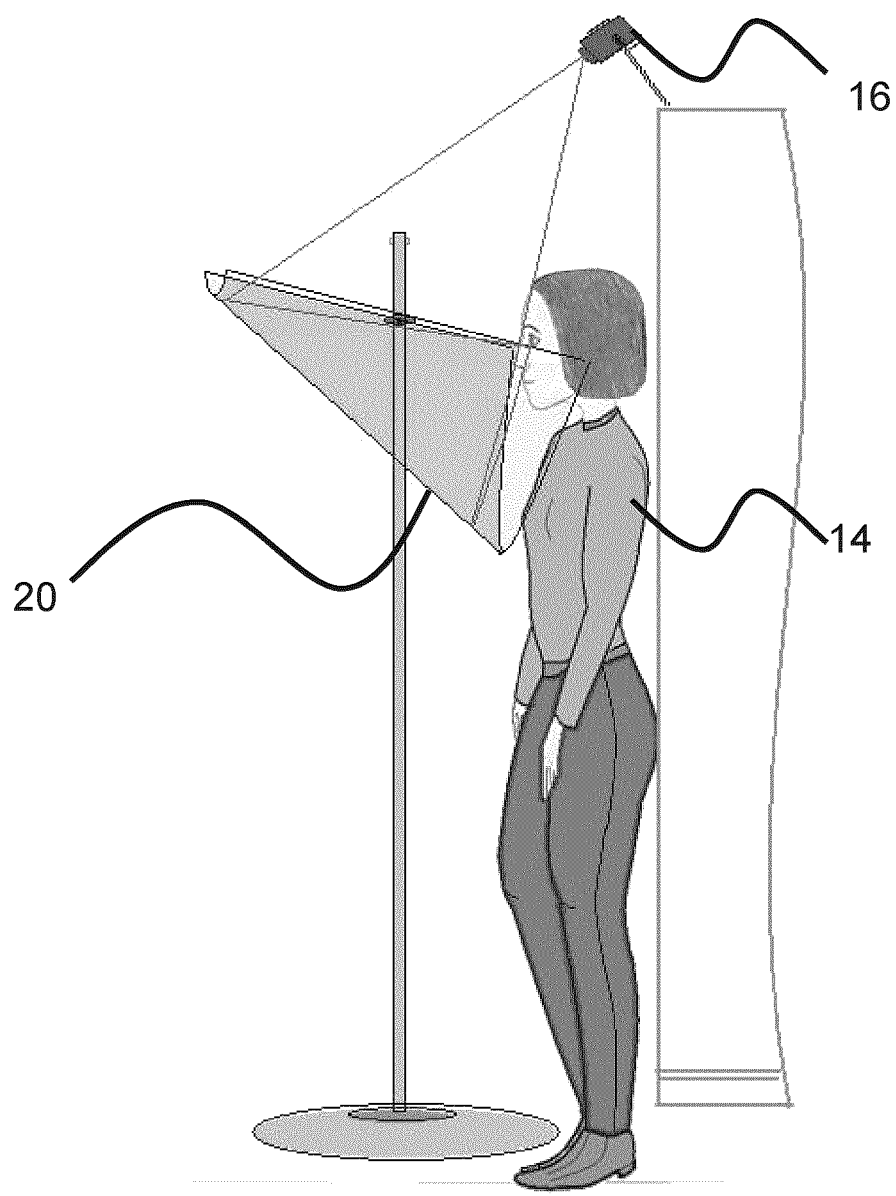
FIG. 4 illustrates a person using a display device according to a third embodiment of the invention.

Such embodiment is illustrated on FIG. 4, where the visual display device comprises a semi-transparent diffusive screen 12 provided in the lower half visual field of the person under test 14. The semi-transparent diffusive screen 20 is arranged so as to diffuse the image projected by a projector 16. As in the previous embodiments, the projector 16 is out of the visual field of the person or masked from the person.

For example, a diffusive screen 20 may be obtained by printing on a transparent plastic sheet a color dot array, for example, light green, red or white patterns.

The transparency factor may be defined geometrically as the specific surface covered by the printed dots. This means that when one hundred dots per square centimeter of surface are printed and that the surface of each dot is 0.001 cm² the transparency factor is TF according to formula (I), $$(100 \text{ dots/cm}^2) \times (0.001 \text{ cm}^2/\text{dot}) = 0.1 = 10\% \tag{I}.$$

Other pattern geometries are possible, such as non-symmetric squares continuous arrays.

Other types of semi-transparent diffusive screens known by the skilled person may be used.

According to a further embodiment described herein, the visual display device may comprise an active photonic screen placed in the lower half of the visual field of the person and arranged to display the dynamic visual pattern. For example, the display device may comprise a LCD screen or a plasma screen or an OLET screen.

During the display step S2, a dynamic visual pattern is displayed on the visual display device.

According to an embodiment described herein, the dynamic visual pattern is displayed with a movement of translation along or rotation around an axis perpendicular to the vertical axis.

The dynamic visual pattern may have an oscillation movement so as to induce greater postural instability.

The dynamic visual pattern may have a periodic movement. Advantageously, having a periodic dynamic visual pattern makes it easier during the measuring step S3 to determine the influence of the dynamic pattern on the postural instability of the person under test.

For example, the dynamic pattern may comprise a checkerboard pattern.

According to different embodiments described herein, the dynamic visual pattern may be geometric, periodic, high contrast pattern, oscillating continuously with a repetitive cadence. The period and/or apparent amplitude may be controlled.

The pattern movement may be presented to the person under test along different spatial axes in reference to the vertical axes.

During the measuring step S3, at least one parameter of the person under test representative of the postural instability is measured. During the measuring step the person under test is required to gaze at a fixed target straight in front of the person while having the dynamic visual pattern displayed on the visual display device.

So as to measure the postural instability of the person under test, such person may be equipped with movement detectors to register the person's balance movements. According to a further embodiment the person under test may be seated or standing on a moving board so as to measure the position of the person's center of pressure of the moving board.

The person's balance movements are influenced by the frequency, amplitude, cadence and the geometry of the dynamic visual pattern, as a natural response to the subject perception of the surrounding space.

Once the body balance movements are registered, it is possible to evaluate the influence and balance perturbation due to the influence of these luminance modulations.

Thus, according to an aspect of the invention, the method according to the invention may be used to measure the effect of a pair of spectacle lenses on body posture stability/instability of a wearer.

The invention has been described above with the aid of embodiments without limitation of the general inventive concept as defined in the claims. In particular, although is some embodiments illustrated in the figure, the person under test is standing or sitting, such illustration such not be considered as a limitation. The person under test may be standing or sitting according to any embodiment of the invention.

The invention claimed is:
1. A method for measuring visually-induced postural instability of a person, the method comprising:
   a display providing step (S1) during which a visual display device comprising a semi-transparent diffusive screen is provided and arranged so as to display a dynamic visual pattern in at least 50% of a lower half visual field of the person and to leave a upper half visual field of the person free,
   wherein the semi-transparent diffusive screen is curved so as to have a conic transversal shape;

a display step (S2) during which the dynamic visual pattern is displayed on the visual display device; and a measuring step (S3) during which a parameter representative of postural instability is measured when the person is gazing at a fixed target straight in front while having the dynamic visual pattern displayed on the visual display device.

2. The method according to claim 1, wherein the dynamic visual pattern is displayed with a movement of translation along or rotating around an axis perpendicular to a vertical axis.

3. The method according to claim 1, wherein the dynamic visual pattern has an oscillating movement.

4. The method according to claim 1, wherein the dynamic visual pattern has a periodic movement.

5. The method according to claim 1, wherein the dynamic visual pattern comprises a checkerboard pattern.

6. The method according to claim 1, wherein the visual display device comprises a dynamic visual pattern generating device adapted to generate the dynamic visual pattern and a projecting device adapted to project the generated dynamic visual pattern on the semi-transparent diffusive screen.

7. The method according to claim 6, wherein reflectivity of the semi-transparent diffusive screen is greater than or equal to 1% and smaller than or equal to 50%.

8. A computer program product stored on computer memory and executed on a processor that when used on computer apparatus causes the processor to process at least one of the steps of claim 1.

9. A non-transitory computer readable medium storing a computer program that when executed by a processor on a computer apparatus causes the processor to carry out one or more sequences of instructions of the computer program product of claim 8.

10. The method of claim 1 further comprising storing a set of data comprising data relating to the postural instability of the person.

11. The method of claim 1 further comprising a set of data comprising data related to the postural instability of the person.

12. The method of claim 1 further comprising storing at least some information obtained relative to the postural instability of the person.

13. A method for measuring influence of a pair of spectacle lenses on body posture stability of a wearer comprising:

measuring visually-induced postural instability of the wearer wearing the pair of spectacle lenses by performing a method comprising:
providing a visual display device comprising a semi-transparent diffusive screen curved so as to have a transversal conic section and arranged to display a dynamic visual pattern in at least 50% of a lower half of a visual field of the wearer;
displaying the dynamic visual pattern on at least a portion of the visual display device; and
measuring at least one parameter representative of postural instability when the wearer is gazing at a fixed target in front of the pair of spectacle lenses while the dynamic visual pattern is displayed on the visual display device.

14. The method of claim 13, wherein one or more of the steps of claim 13 is provided on a computer program product stored on a computer memory and executed on a processor that when used on a computer apparatus causes the processor to carry out at least a portion of the method of claim 13.

15. The method of claim 14, wherein the computer program product is stored on a non-transitory computer readable medium that when executed by the processor on the computer apparatus causes the processor to execute at least a portion of the method of claim 13.

16. The method of claim 13, further comprising a set of data comprising data relating to the postural instability of the person.

17. A device for measuring visually-induced postural instability of a person, the device comprising:
a fixed target arranged straight in front of the person;
a semi-transparent diffusive screen placed in the lower half visual field of the person,
wherein the semi-transparent diffusive screen in curved so as to have a conic transversal shape,
wherein the reflectivity of the semi-transparent screen is greater than or equal to 1% and smaller than or equal to 50%;
a visual display device configured and arranged so as to display a dynamic visual pattern in at least 50% of a lower half visual field of the person and to leave a upper half visual field of the person free, the visual display device comprising:
a dynamic visual pattern generating device adapted to generate the dynamic visual pattern; and
a projecting device adapted to project the generated dynamic visual pattern on the semi-transparent diffusive screen placed in the lower half visual field of the person and arranged so that the person visualizes the dynamic visual pattern on the semi-transparent diffusive screen,
wherein the dynamic visual pattern comprises at least one of:
a movement of translation along an axis perpendicular to a vertical axis,
a movement of translation rotating around the axis perpendicular to the vertical axis,
a checkerboard pattern,
an oscillating movement, and
a periodic movement; and
a measuring means configured to measure a parameter representative of postural instability of the person when the person is gazing at the fixed target straight in front while having the dynamic visual pattern displayed on the visual display device.

* * * * *